United States Patent [19]

Conklin

[11] Plant 4,441

[45] Jul. 24, 1979

[54] ROSE PLANT

[76] Inventor: H. A. Conklin, P.O. Box 365, McFarland, Calif. 93250

[21] Appl. No.: 927,615

[22] Filed: Jul. 21, 1978

[51] Int. Cl.[2] ..... A01H 5/00

[52] U.S. Cl. ..... Plt./2

[58] Field of Search ..... Plt./2

*Primary Examiner*—Robert E. Bagwill

[57] ABSTRACT

A climbing rose plant of the hybrid tea class combining red, cerise, and yellow petal colors, originating as a sport of Patchwork.

1 Drawing Figure

1

The present invention relates to a new and distinct variety of rose plant of the climbing hybrid tea class, which originated as a sport of the variety, "Patchwork" (U.S. Plant Pat. No. 4,012).

The new variety was discovered by me at my nursery in McFarland, Calif., in a cultivated area. My attention was drawn to a plant that was presumed to be the variety, Patchwork, but which exhibited definite climbing characteristics in that it produced canes which were 8 to 10 feet in length. This new variety has been asexually reproduced by budding, under my supervision, at McFarland, Calif. Observations of the above asexual reproductions of the new variety have shown that the climbing habit comes true to form and is transmissible through succeeding asexual propagations.

2

The accompanying drawing shows a specimen plant of the new variety which is illustrative of the typical climbing habit of growth.

In view of the fact that the new variety is distinguished from its parent only by its climbing habit of growth, it is unnecessary to describe the new variety in detail, since it conforms substantially to the detailed description appearing in U.S. Plant Pat. No. 4,012 dated Jan. 25, 1977, to which reference may be readily had.

I claim:

1. A new and distinct variety of rose plant of the climbing hybrid tea class, substantially as herein shown and described, characterized particularly as to novelty by its general similarity to its parent variety, Patchwork (U.S. Plant Pat. No. 4,012), but different therefrom by its pronounced climbing growth habit.

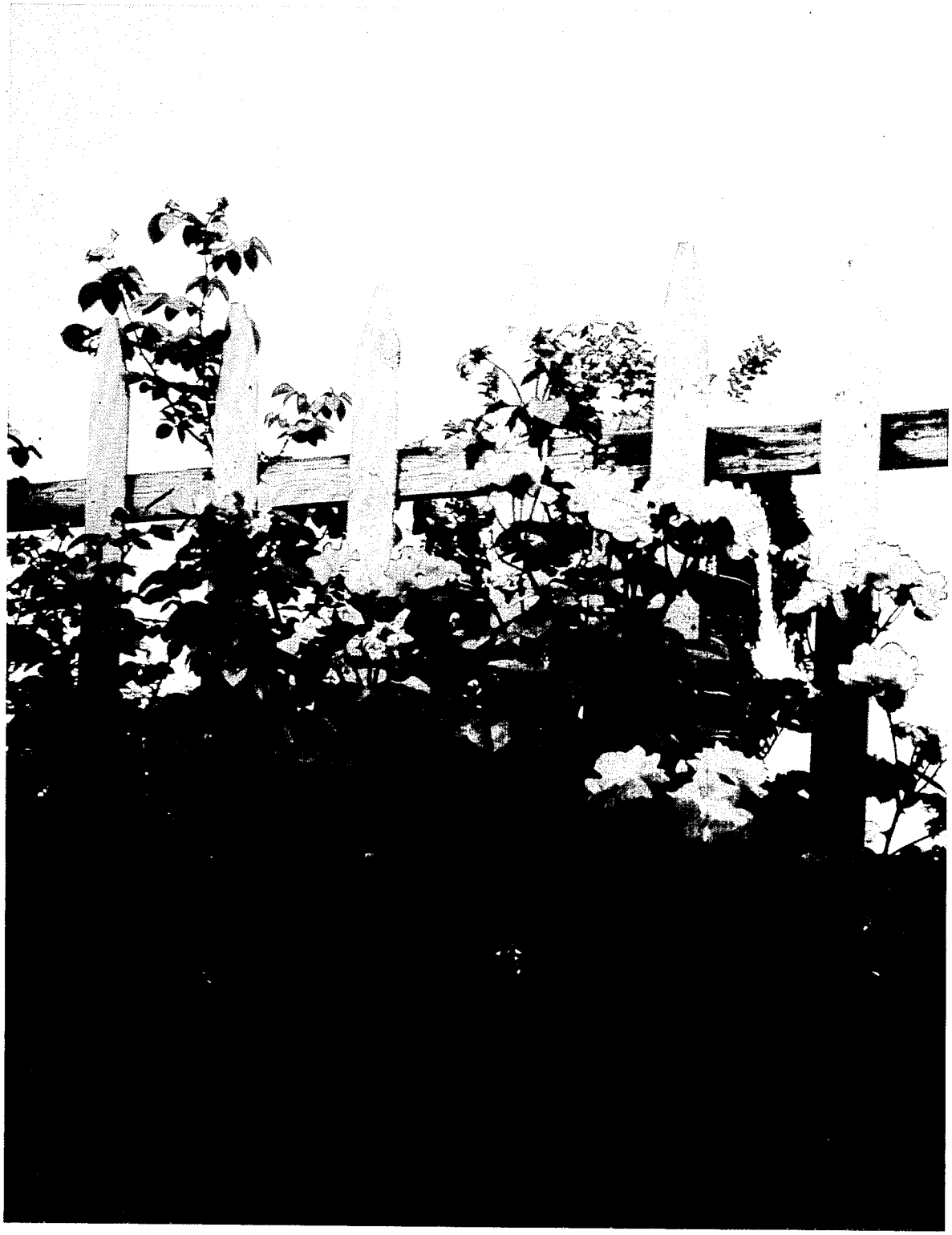

* * * * *